US008082017B2

(12) United States Patent  (10) Patent No.: US 8,082,017 B2
Messerges et al.  (45) Date of Patent: Dec. 20, 2011

(54) METHOD AND APPARATUS FOR MEASURING CAPILLARY REFILL TIME AND CARRYING OUT PULSE OXIMETRY WITH A SINGLE DEVICE

(75) Inventors: Joanne L. Messerges, Wauwatosa, WI (US); George M. Hutchinson, Milwaukee, WI (US)

(73) Assignee: The General Electric Company, Schenectady, NY (US)

( * ) Notice: Subject to any disclaimer, the term of this patent is extended or adjusted under 35 U.S.C. 154(b) by 1532 days.

(21) Appl. No.: 11/445,717

(22) Filed: Jun. 2, 2006

(65) Prior Publication Data

US 2007/0282182 A1    Dec. 6, 2007

(51) Int. Cl.
 *A61B 5/1455*  (2006.01)
 *A61B 5/02*  (2006.01)
(52) U.S. Cl. ........ 600/324; 600/323; 600/335; 600/340; 600/483; 600/504
(58) Field of Classification Search .......... 600/309–344, 600/481, 500, 501
See application file for complete search history.

(56) References Cited

U.S. PATENT DOCUMENTS

| 3,698,382 | A | * | 10/1972 | Howell | 600/481 |
| 4,883,055 | A | * | 11/1989 | Merrick | 600/335 |
| 5,203,342 | A | * | 4/1993 | Sakai | 600/323 |
| 5,827,181 | A | * | 10/1998 | Dias et al. | 600/322 |
| 6,400,972 | B1 | * | 6/2002 | Fine | 600/322 |
| 6,466,808 | B1 | * | 10/2002 | Chin et al. | 600/323 |
| 6,587,704 | B1 | * | 7/2003 | Fine et al. | 600/335 |
| 6,685,635 | B2 | | 2/2004 | Shani et al. | |
| 6,983,178 | B2 | * | 1/2006 | Fine et al. | 600/335 |
| 7,254,432 | B2 | * | 8/2007 | Fine | 600/335 |
| 7,483,733 | B2 | * | 1/2009 | Shani et al. | 600/476 |

* cited by examiner

*Primary Examiner* — Eric Winakur
*Assistant Examiner* — Chu Chuan (JJ) Liu
(74) *Attorney, Agent, or Firm* — Andrus, Sceales, Starke & Sawall, LLP

(57) ABSTRACT

A device for measuring the capillary refill time and blood oxygenation includes light sources and a light detector. The device also includes an actuator for applying pressure to a selected portion of the body of the patient, such as the nail bed of a finger or toe of the patient, to cause the removal of blood from the nail bed when actuated. A timer commences a time interval with a deactuation of the actuator. The deactuation relieves the pressure applied by the actuator to the body portion of the patient and allows blood to return to the portion. The timing interval is terminated by a reduction in the amount of light received by the light detector as a result of the restoration of blood to the body portion. The time interval so determined comprises an indication of the capillary refill time of the patient.

20 Claims, 3 Drawing Sheets

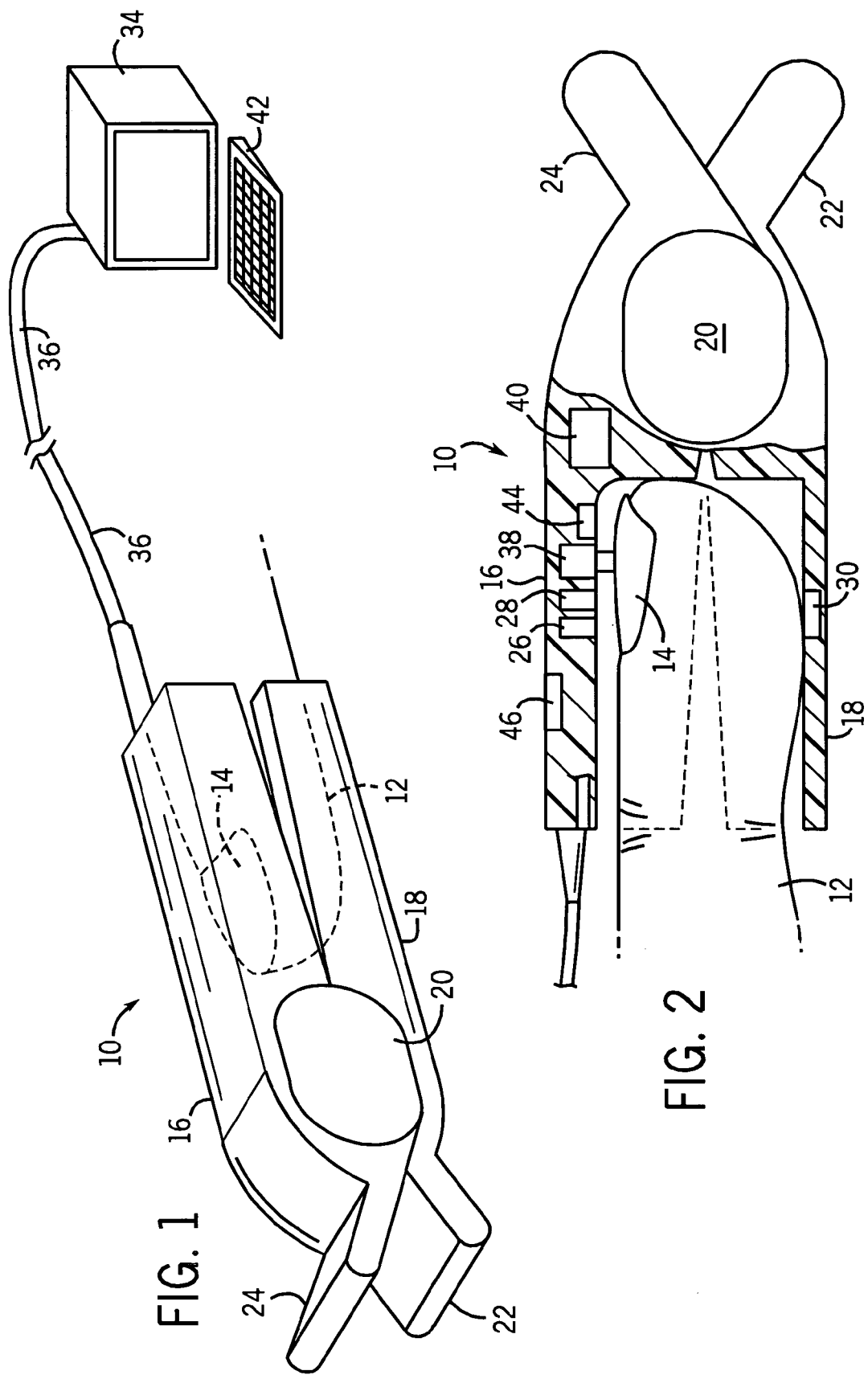

METHOD AND APPARATUS FOR MEASURING CAPILLARY REFILL TIME AND CARRYING OUT PULSE OXIMETRY WITH A SINGLE DEVICE

FIELD OF THE INVENTION

The present invention relates to a measurement device that can be used to both measure the capillary refill time of a patient as well as to carry out pulse oximetry.

BACKGROUND OF THE INVENTION

Capillary refill time (CRT), also known as capillary filling time, is a clinically accepted measure of the amount of blood flow, or perfusion, to tissue occurring in a patient. It can provide a quick indication of how well the patient's vascular system is functioning, as well as the state of hydration/dehydration of the patient. A clinician typically measures capillary refill time by applying pressure to a fingernail or toenail of the patient until the nail bed under the fingernail or toenail turns white or blanches. This indicates that blood has been forced from the bed tissue. The pressure is then released and the time required for the nail bed tissue to regain its original color is measured. A time interval of two seconds or less is ordinarily taken as an indication that the patient's vascular system functioning and hydration is normal.

While apparatus is known in the prior art for carrying out the measurement of capillary refill time, as in U.S. Pat. No. 6,685,635, such apparatus has not found wide acceptance. Thus, at the present time in standard clinical practice, capillary refill time measurements are usually completely manual in nature. That is, the clinician must decide when to take a capillary refill time measurement, carry out the steps necessary to make the measurement, record or remember the measured capillary refill time, and, if applicable, trend the values over time. These circumstances increase the clinician's physical and mental workload and present opportunities for errors and omissions. The information is often in analog form, i.e. patient chart entries, so that collection and statistical treatment of the information by computer becomes more difficult.

Pulse oximetry is another commonly used technique for assessing the condition of a patient's circulatory system. Pulse oximetry measures the amount of oxygen in a patient's blood, specifically, the extent of oxygen saturation ($SpO_2$) of arterial hemoglobin in the blood.

A pulse oximeter has two basic components. One is an electro-optical sensor, or probe, that is applied to the patient. A number of body locations may be used for this purpose. The probe may be placed on a finger or toe of the patient as well as on the nose, forehead, or earlobe of the patient can also be used. The probe has two light sources, each generating light of a different wavelength in the red-orange spectral range. The light is applied to patient's tissue and received by a light detector that measures the amount of light that has not been absorbed by blood hemoglobin in the tissue. The light detector is connected to the second component of the pulse oximeter, namely, a signal processor that computes oxygen saturation ($SpO_2$) based on the ratio of the amount of light of each wavelength sensed by the detector. The signal processor distinguishes hemoglobin saturation in arterial blood from that in venous and capillary blood by sensing the pulsatile nature of the former thus giving rise to the term "pulse" oximetry.

Pulse oximeters have been used to provide an indication of tissue perfusion by taking the ratio of the pulsatile to non-pulsatile components in a plethysmographic signal of the pulse oximeter. Changes in the perfusion index (PI) so formed, over time, may quantify peripheral perfusion by indirectly monitoring changes in arterial blood flow. However, capillary refill time is a more direct and immediate measurement of tissue perfusion.

It would therefore be advantageous to have a single device that could measure multiple parameters relating to the vascular system of a patient, namely capillary refill time and arterial blood hemoglobin oxygen saturation.

SUMMARY OF THE INVENTION

An embodiment of the present invention provides a single device capable of measuring multiple, clinically useful parameters of a patient. More specifically, the device combines a measurement of capillary refill time with that of arterial oxygen saturation of the blood.

The device, and the method, of embodiments of the present invention are capable of automating such measurements so as to ensure that periodic measurements are carried out in a timely fashion and to automatically record and statistically treat periodic determinations, particularly, of capillary refill time. The device of the present invention is simple and economical in construction and use and the method is easy to carry out. The device can be applied and the method carried out at a number of patient body locations thereby to adapt to the circumstances of a particular patient and lend a desirable flexibility in obtaining pulse oximetry and capillary refill time measurements.

Briefly, an embodiment of the invention comprises a device for measuring the capillary refill time of a patient and for use in determining an amount of oxygen in the blood of the patient. The device has light sources and a light detector for use in carrying out pulse oximetry. The device also includes an actuator for applying pressure to a selected portion of the patient's body at which the application of pressure to the portion will cause a removal of blood from the tissue of the portion. For example, the actuator may apply pressure to the nail bed of a nail of a finger or toe of the patient to cause the removal of blood from the nail bed and thus a whitening or blanching of the nail bed tissue. A control means is coupled to the actuator for controlling its actuation and deactuation and thus a whitening or blanching of the nail bed tissue. The control means is also coupled to the light detector for determining the amount of light received by the light detector. A timer is coupled to the control means for determining a time interval that is commenced with a deactuation of the actuator. The deactuation relieves pressure previously applied by the actuator to the portion of the patient's body and allows blood to return to the portion. The timing interval is terminated by a reduction in the amount of light received by the light detector as a result of the restoration of blood to the body portion. The time interval so determined comprises an indication of the capillary refill time of the patient. The device also includes a temperature detector for compensating the indication of capillary refill time in accordance with a skin temperature measurement proximate to the body portion of the patient used to determine capillary refill time.

An embodiment of the present invention also comprises a method for determining the capillary refill time of a patient utilizing apparatus that is also suitable for carrying out pulse oximetry. Light is applied to a selected portion of the patient's body, such as a nail bed of a patient's fingernail or toenail using a pulse oximetry light source. The selected portion is compressed by an actuator in the apparatus to cause removal of blood from the portion. Thereafter, the actuator is deactuated to allow restoration of blood to the portion. A timing interval is commenced upon deactuation of the actuator. The amount of light received by a light detector suitable for carrying out pulse oximetry is measured following deactuation of the actuator. The timing interval is terminated based on a reduction in the amount of light received by the light detector as a result of the restoration of blood to the selected body portion. The timing interval is an indication of the capillary refill time of the patient. The skin temperature of the patient proximate to the selected portion may be measured and the indication of capillary refill time altered based on the measured skin temperature.

The present invention will be further understood by reference to the following detailed description taken in conjunction with the drawing.

BRIEF DESCRIPTION OF THE DRAWINGS

FIG. 1 is a perspective view of an embodiment of the device of the present invention.

FIG. 2 is a cross-sectional view of the device of FIG. 1.

DETAILED DESCRIPTION OF THE PREFERRED EMBODIMENTS

Figure 3:
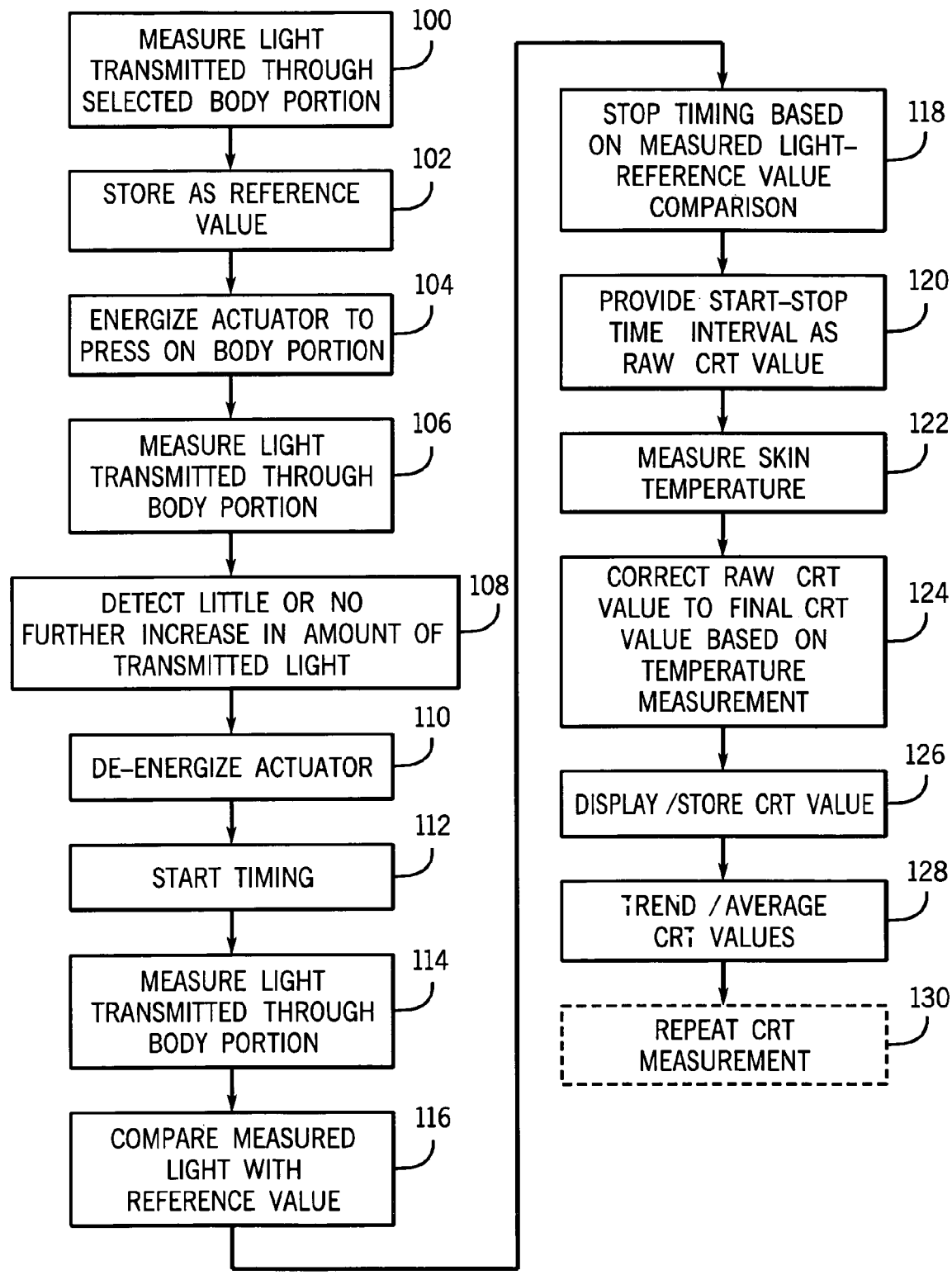
FIG. 3 is a flow chart of the operation of the device.

FIG. 1 shows an embodiment of device 10 of the present invention for carrying out pulse oximetry and measuring capillary refill time of a patient. Device 10 is suitable for being placed on a selected portion of the body of the patient. As noted above, such portions include those in which blood can be removed from the tissue of the portion by the application of pressure. The selected portion is exemplarily shown as in FIGS. 1 and 2 as finger 12. When device 10 is in place, a portion of the device will be above fingernail 14 and a portion will be positioned at the end of the finger below the fingernail. Device 10 includes a first member 16 and a second member 18 joined by spring loaded hinge 20 urging the members into a condition of contiguity. A clinician opens members 16 and 18 to allow device 10 to be placed on finger 12 by squeezing extensions 22 and 24 of members 16 and 18, respectively, and thereafter releasing the extensions to clamp device 10 on finger 12 so that the device embraces the finger of the patient.

As shown most clearly in FIG. 2 first member 16 includes light sources 26, 28 suitable for use in pulse oximetry measurement. In a typical pulse oximeter, one of the light sources will generate light having a wavelength of about 660 nm and the other light source will generate light having a wavelength of about 930 nm. Light sources 26 and 28 shine light onto the tissue of patient's finger 12. A blood oxygen saturation measurement may use either light transmitted through the patient's finger or light reflected from the patient's finger. FIG. 2 shows an arrangement using transmitted light. For this purpose, light detector 30 is provided in second member 18 to receive light passing through finger 12.

Light sources 26, 28 and light detector 30 are connected to a signal processing circuitry for detecting arterial blood oxygen saturation. It is typical to employ a microprocessor in a separate computer or monitor 34 connected to device 10 by cable 36 for this purpose. Cable 36 also provides power to light sources 26, 28 and obtains the signal from light detector 30 for provision to monitor 34.

For obtaining an indication of capillary refill time, first member 16 includes actuator 38, such as a solenoid having a wire coil or winding surrounding a magnetic slug or armature and forming a linear actuator. Energizing the winding with electric current causes extension of the armature out of the coil and member 16 in the manner shown in FIG. 2. Actuator 38 is mounted in member 16 so that it will be positioned over fingernail 14 of finger 12 when device 10 is affixed to the finger 12 of the patient. For controlling actuator 38, it may be connected to microprocessor 40 in member 16 or, via cable 36 to a corresponding microprocessor in monitor 34. The operation of the microprocessor is, in turn, controlled by an appropriate user interface, such as a keyboard 42 for monitor 34 or suitable switches on member 16 associated with microprocessor 40. The winding of actuator 38 is connected to an appropriate source of electrical energization, such as via cable 36 from monitor 34.

Member 16 also includes temperature sensor 44 for measuring the patient's skin temperature proximate to nail 14. Temperature sensor 44 is connected to the microprocessor used with device 10.

In the operation of device 10, the measurement of arterial blood hemoglobin oxygen saturation ($SpO_2$) is carried out in a conventional manner using the amount and pulse characteristics of the light from light sources 26 and 28 received by light detector 30 and the signal processing circuitry in monitor 34.

The measurement of capillary refill time is carried out in the following manner, as shown by the flow chart of FIG. 3, as controlled by/employing microprocessor 40 or the signal processing circuitry in monitor 34.

Light sources 26 and 28 and light detector 30 are used to obtain a signal corresponding to the amount of light transmitted through the tissue of the selected patient body portion, such as the patient's finger and nail bed. See step 100 of FIG. 3. One or both of the light sources may be utilized. As noted above, the amount of transmitted light comprises that which is not absorbed by the blood in the tissue of the patient's finger or other body portion. A signal value corresponding to this measured amount is stored in an appropriate memory associated with microprocessor 40 or the signal processing circuitry of monitor 34. This occurs in step 102 and the stored amount serves as a reference value for the capillary refill time measurement.

Pressure is then applied to the body portion by energizing actuator 38 in step 104. The measurement amount of transmitted light continues in step 106. The pressure applied by linear actuator 38 will force the blood out of the capillaries of the selected body portion. The removal of blood from the tissue will reduce the absorbance of light from light source(s) 26/28 by the tissue of the patient, causing the amount of light transmitted to light detector 30 to increase. When the amount of transmitted light received by light detector 30 has increased to a point where it shows little or no further increase, it is an indication that blood that has been forced from the selected body portion. This is carried out in step 108. Actuator 38 is then de-energized at step 110 and a timer in microprocessor 40 or in the signal processing circuitry of monitor 34 started at step 112. As blood circulation returns to the body portion of the patient, the amount of transmitted light from light source(s) 26/28 received by light detector 30 will decrease as more light is absorbed by the returning blood. The amount of transmitted light is measured in step 114. A signal value corresponding to the transmitted light measured in step 114 is compared with the stored value obtained in step 102. This is carried out in step 116 as in a comparator associated with microprocessor 40 or the signal processing circuitry of monitor 34. When the light measured in step 114 compares well to the stored value obtained in step 102, the timing interval is stopped at step 118. While it is possible to use an exact comparison of the transmitted light measured in step 114 with the stored value, the nature of the restoration of blood circulation to a body portion such as the nail bed of nail 14 is of a nature that it is deemed more practical to terminate the timing interval in step 118 when the amount of transmitted light measured in step 114 approximates the stored value obtained in step 102 as by being within a quantitative range or percentage, such as when the amount of light measured in step 114 attains a value equaling 75% of the stored value obtained in step 102.

The timing interval between timing initiation in step 112 and timing termination in step 118 comprises a raw indication of the capillary refill time of the patient. See step 120.

The skin temperature of the patient proximate to the selected body portion such as nail 14 affects the capillary refill time in that as skin temperature increases, capillary refill time also tends to increase. For this reason, a skin temperature measurement is made at step 122 using temperature sensor 44 and the raw indication of capillary refill time corrected on the basis of the temperature measurement, in step 124, to provide a final capillary refill time value. The final capillary refill time may be displayed and/or stored in step 126. Display 46 on device 10 or the display of monitor 34 may be used to show the capillary refill time.

The capillary refill time value obtained in step 124 will typically comprise a digital value. The digital value is stored, as in microprocessor 40 or the signal processing circuitry of monitor 34, in step 126, to provide a record of the measurement and for comparison to previous values to allow trending, averaging, or other statistical analysis of capillary refill times in step 128 for use by the attending clinician.

The measurement of capillary refill times may be automatically initiated at periodic intervals under the control of microprocessor 40 or the signal processing circuitry of monitor 34, as shown at step 130 of FIG. 3. The storage, manipulation, and automatic restart relieves the clinician of the need to manually store, statistically treat, and repeat capillary refill time measurements.

Figure 4:
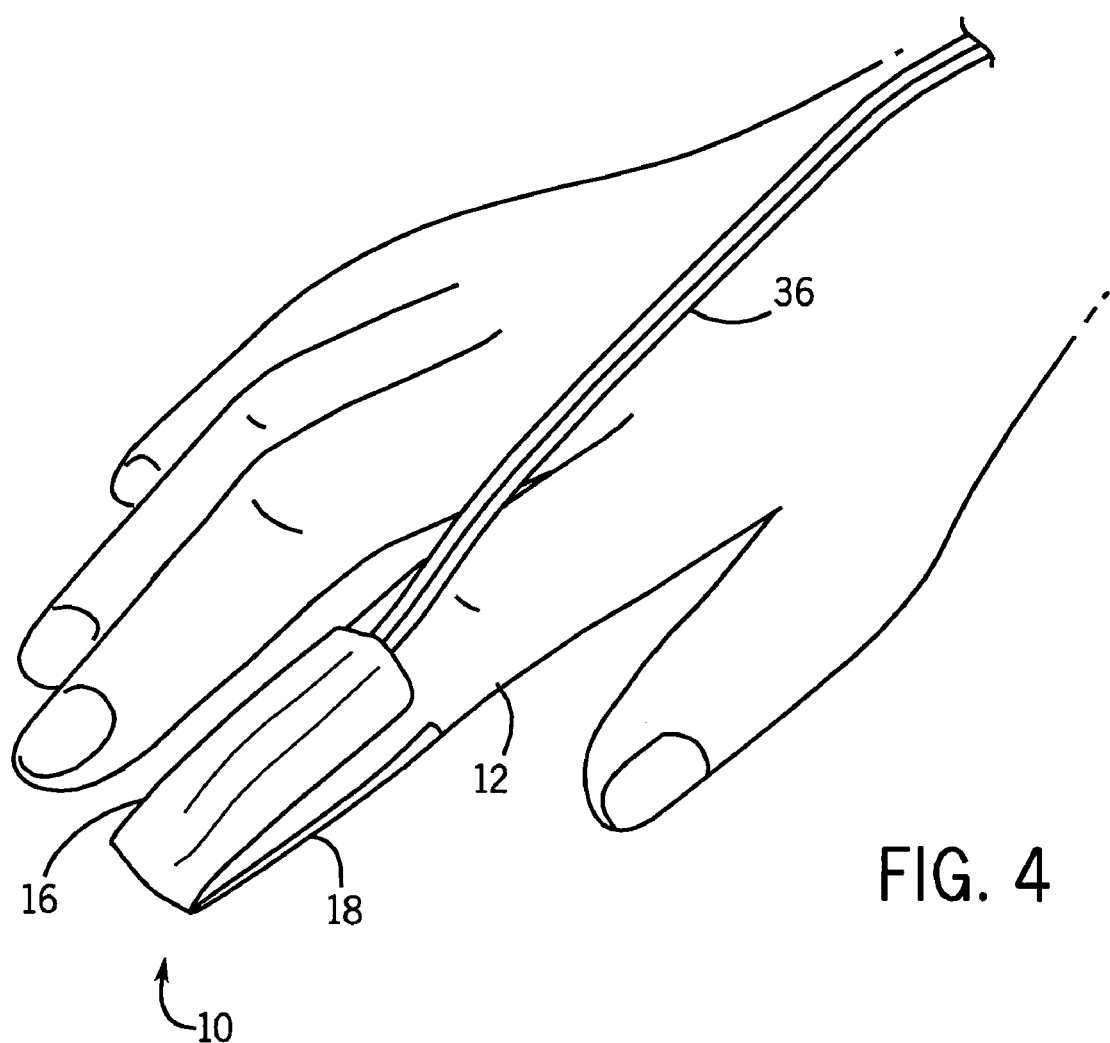
FIG. 4 is a perspective view of another embodiment of the device of the present invention.

While FIGS. 1 and 2 show a pulse oximeter probe that clamps on the selected body portion of the patient, other types of pulse oximetry probes are adhesively affixed to a portion of the patient, as shown in FIG. 4. Also, while the actuator and temperature sensing elements used to obtain the capillary refill time measurement have been described, above, as integral with a device also forming a pulse oximetry probe, actuator 38, microprocessor 40, and temperature sensor 44 may comprise an attachment to the portions of the device used for pulse oximetry, if desired. Still further, while the foregoing describes the device and method of the present invention as using transmitted light, they may, as noted above, instead use reflected light.

Various alternatives and embodiments are contemplated as being within the scope of the following claims particularly pointing out and distinctly claiming the subject matter regarded as the invention.

What is claimed is:

1. A device for measuring the capillary refill time of a patient and for use in determining an amount of oxygen in the blood of the patient by pulse oximetry, said device comprising:
   a first member and a second member movably secured to each other, the first and second members configured to secure to opposed sides of a selected portion of the body of the patient;
   a first light source providing light at a first wavelength and a second light source providing light at a second wavelength, the first and second light sources secured in the first member and positioned to apply light to the selected portion of the body of the patient;
   a light detector positioned to receive light from the first and second light sources at least partially transmitted through the selected portion of the body of the patient;
   an actuator connected to the first member and second member that when actuated causes the first member and second member to compress the selected portion and cause removal of blood from the selected portion, the pressure being relieved when the actuator is deactuated to allow restoration of blood to the tissue of the portion;
   a controller coupled to said actuator and to said light detector, the controller operates the actuator to actuate and deactuate the actuator and determines an amount of light received by said light detector that has been provided by the first light source and second light source wherein the controller deactuates the actuator when the amount of light received by said light detector reaches a steady state, the controller further determines an amount of oxygen in the blood of the patient by pulse oximetry from the amount of light received by the light detector from the first and second light sources; and
   a timer coupled to the controller that determines a time interval wherein the controller commences the time interval measured by the timer upon deactivation of said actuator and terminates the time interval measured by the timer in response to a reduction in the amount of light from the first and second light sources received by said light detector as a result of the restoration of blood to the selected body portion, the time interval comprising an indication of the capillary refill time of the patient.

2. The device according to claim 1 further including a comparison means coupled to said timer for terminating the time interval by comparing a signal value of the amount of light received by said light detector following deactuation of said actuator with a stored value.

3. A device according to claim 2 wherein said comparison means is further defined as carrying out a comparison using a stored value comprising a measurement of the amount of light received by said light detector prior to actuating said actuator.

4. A device according to claim 2 further including a memory means for storing said stored value.

5. A device according to claim 1 wherein said controller is further defined as deactuating said actuator responsive to a characteristic of an increased amount of light received by said light detector following actuation of said actuator.

6. A device according to claim 1 wherein said controller is further defined as deactuating said actuator when increases in the amount of light received by said light detector lessen or no longer occur.

7. A device according to claim 1 further including a temperature sensor for measuring skin temperature of the patient proximate to the selected body portion, the indication of capillary refill time being altered in accordance with the measured temperature.

8. A device according to claim 1 wherein said controller comprises a microprocessor.

9. A device according to claim 1 wherein said actuator forms an integral component of said device.

10. A device according to claim 1 wherein said actuator comprises an attachment for said device.

11. A device according to claim 1 wherein the first wavelength is about 660 nanometers and the second wavelength is about 930 nanometers.

12. A device according to claim 1 wherein said device employs light reflected from the tissue of the patient.

13. A device according to claim 1 wherein the first and second light sources apply light to the nail bed of a finger or toe of the patient and said actuator applies pressure to the nail of the patient when actuated.

14. A device for measuring the capillary refill time of a patient and for use in determining an amount of oxygen in the blood of the patient by pulse oximetry, said device comprising:
 a first member and a second member movably connected to each other, the first and second members configured to secure to opposed sides of a selected portion of the body of the patient;
 a first light source and a second light source secured to the first member, wherein the first light source produces light with a wavelength of about 660 nanometers and the second light source produces light with a wavelength of about 930 nanometers;
 a light detector secured to the second member, the light detector receives light transmitted through the selected portion from the first and second light sources
 an actuator that operates the first and second members to apply pressure to the selected portion to compress the selected portion and cause removal of blood from the selected portion to allow restoration of blood to the selected portion;
 a controller coupled to said actuator for controlling the actuation and deactuation of said actuator, said controller being coupled to said light detector for determining the amount of light received by said light detector, said controller deactuates said actuator when the controller determines a steady state in a determined increased amount of light received by said light detector as a result of actuation of said actuator, the controller further determines an amount of oxygen in the blood of the patient calculated from the light received by the light detector from the first and second light source; and
 a timer coupled to said controller, the controller operates the timer to determine a time interval that is commenced with a deactuation of said actuator and is determined upon a comparison of a signal value of the amount of light received by said light detector following deactuation of said actuator with a stored value comprised of a measurement of the amount of light received by said light detector prior to actuating said actuator, and the time interval provides an indication of the capillary refill time of the patient; and
 a temperature sensor coupled to the controller, the temperature sensor measures skin temperature of the patient proximate to the nail, and the controller alters the indication of capillary refill time in accordance with the measured temperature.

15. A method for determining the capillary refill time of a patient utilizing apparatus suitable for carrying out pulse oximetry, said method comprising the steps of:
 applying a first wavelength of light and a second wavelength of light to a selected portion of the body of the patient and the application of light being carried out using a first light source and a second light source;
 receiving the first wavelength of light and the second wavelength of light with a light detector;
 measuring at least an amount of light received by the light detector;
 determining an amount of oxygen in the blood of the patient by pulse oximetry from at least the first and second wavelength of light received by the light detector and the measured amount of light;
 storing the measured amount of received light as a reference value;
 actuating an actuator to compress the selected body portion of the patient to cause removal of blood from the tissue of the patient;
 measuring an amount of light received by the light detector with the patient's body portion in the compressed condition;
 detecting changes in the amount of received light resulting from the compression of the patient's body portion;
 deactuating the actuator responsive to the changes in the amount of received light;
 starting a timing interval upon deactuating the actuator;
 measuring an amount of received light following deactuation of the actuator;
 comparing the amount of light received following deactuation with the reference value;
 stopping the timing interval based on the comparison of the light received following deactuation with the reference value; and
 providing the time interval as an indication of the capillary refill time of the patient.

16. A method according to claim 15 further comprising deactuating the actuator responsive to a lessening or termination of increases in the amount of received light.

17. A method according to claim 15 wherein the method employs light transmitted through the tissue of the patient.

18. A method according to claim 15 wherein the method employs light reflected from the tissue of the patient.

19. A method according to claim 15 further defined as including the steps of measuring the skin temperature of the patient and altering the indication of capillary refill time based on the measured skin temperature of the patient.

20. A method according to claim 15 wherein the step of applying light is further defined as applying light to a nail bed of a nail of a patient's finger or toe and the step of actuating the actuator is further defined as compressing the nail bed of the nail of the patient's finger or toe.

* * * * *